(12) United States Patent
Kotian et al.

(10) Patent No.: US 9,016,560 B2
(45) Date of Patent: Apr. 28, 2015

(54) COMPONENT IDENTIFICATION SYSTEM

(71) Applicant: General Electric Company, Schenectady, NY (US)

(72) Inventors: Shyamanth Kotian, Bangalore (IN); Srivatsa Dhanvantri, Bangalore (IN); John David Ward, Jr., Woodruff, SC (US)

(73) Assignee: General Electric Company, Schenectady, NY (US)

( * ) Notice: Subject to any disclaimer, the term of this patent is extended or adjusted under 35 U.S.C. 154(b) by 138 days.

(21) Appl. No.: 13/863,209

(22) Filed: Apr. 15, 2013

(65) Prior Publication Data

US 2014/0306003 A1    Oct. 16, 2014

(51) Int. Cl.
| | | |
|---|---|---|
| *G06F 17/00* | (2006.01) | |
| *G06F 17/30* | (2006.01) | |
| *F01D 21/00* | (2006.01) | |
| *G02B 23/24* | (2006.01) | |
| *G01N 21/95* | (2006.01) | |
| *G06K 7/14* | (2006.01) | |
| *G06Q 10/06* | (2012.01) | |
| *G06Q 10/08* | (2012.01) | |
| *G06Q 50/28* | (2012.01) | |

(52) U.S. Cl.
CPC ............ *G06F 17/30* (2013.01); *F01D 21/003* (2013.01); *G02B 23/24* (2013.01); *F05D 2230/72* (2013.01); *F05D 2260/83* (2013.01); *G01N 21/95* (2013.01); *G06K 7/1417* (2013.01); *G06Q 10/06* (2013.01); *G06Q 10/08* (2013.01); *G06Q 50/28* (2013.01)

(58) Field of Classification Search
USPC .......................................... 235/375; 600/103
See application file for complete search history.

(56) References Cited

U.S. PATENT DOCUMENTS

| | | | |
|---|---|---|---|
| 4,980,763 | A | 12/1990 | Lia |
| 4,998,166 | A | 3/1991 | Salvati |
| 5,573,492 | A | 11/1996 | Dianna et al. |
| 5,638,164 | A | 6/1997 | Landau |
| 6,748,112 | B1 | 6/2004 | Nguyen et al. |
| 6,827,275 | B2 | 12/2004 | Allen |
| 6,992,315 | B2 | 1/2006 | Twerdochlib |
| 7,170,677 | B1 | 1/2007 | Bendall et al. |
| 7,214,947 | B2 | 5/2007 | Bueno et al. |

(Continued)

FOREIGN PATENT DOCUMENTS

| | | |
|---|---|---|
| JP | 2003184503 A | 7/2003 |
| JP | 2003184509 A2 | 7/2003 |
| WO | 2013045108 A1 | 4/2013 |

OTHER PUBLICATIONS

European Search Report and Written Opinion from EP Patent Application No. 14164696.8 dated Jul. 18, 2014.

*Primary Examiner* — Daniel Hess
(74) *Attorney, Agent, or Firm* — Ernest G. Cusick; Hoffman Warnick LLC

(57) ABSTRACT

A component identification system for identifying an industrial machine component in situ is disclosed herein. In an embodiment, a computer system is provided which is configured to implement a method of identifying a component of an industrial machine in situ. In particular, the computer system is configured to decode an image containing a data matrix code, and identify the data matrix code in the image. The computer system is further configured to associate the data matrix code in the image with an identified component in a database.

16 Claims, 3 Drawing Sheets

(56) References Cited

U.S. PATENT DOCUMENTS

| | | |
|---|---|---|
| 7,336,197 B2 | 2/2008 | Ding et al. |
| 7,489,811 B2 | 2/2009 | Brummel et al. |
| 7,518,632 B2 | 4/2009 | Konomura |
| 7,552,647 B2 | 6/2009 | Soechting et al. |
| 7,553,274 B2 | 6/2009 | Miyake et al. |
| 7,656,445 B2 | 2/2010 | Heyworth |
| 7,713,192 B2 | 5/2010 | Murata |
| 8,027,095 B2 | 9/2011 | Havens |
| 8,169,478 B2 | 5/2012 | Nadabar et al. |
| 8,189,044 B2 | 5/2012 | Stier |
| 8,352,117 B2 | 1/2013 | Martin |
| 2003/0094493 A1 | 5/2003 | Guerrero et al. |
| 2004/0183900 A1 | 9/2004 | Karpen et al. |
| 2007/0059162 A1 | 3/2007 | Nolfi et al. |
| 2007/0132840 A1 | 6/2007 | Konomura |
| 2009/0314205 A1 | 12/2009 | Patalay et al. |
| 2010/0287906 A1 | 11/2010 | Xia et al. |
| 2011/0267451 A1 | 11/2011 | Drescher et al. |
| 2013/0345502 A1* | 12/2013 | Mitsunaga .................... 600/103 |

\* cited by examiner

COMPONENT IDENTIFICATION SYSTEM

BACKGROUND OF THE INVENTION

The invention relates generally to machines having an external casing. More particularly, the invention relates to in situ identification of components of machines having an external casing.

Many types of industrial machines such as turbines, include critical components which are encased within an external casing or shell. During the life cycle of a machine, these critical components may require inspection, repair, or maintenance in order to maximize the lifespan of the parts and the machine as a whole.

Tracking of component condition, repair status, and other details appurtenant to inspections is also desirable. To aid in this, industrial machine components may be stamped with identifiers, and cataloged in a database. During disassembly for repair and/or inspection, components may be removed from the industrial machine and their identification codes may be scanned. The scanned identification code may be compared with the database of components, and the part being scanned may be identified. However, this solution still requires the disassembly of the industrial machine in order to access the identification code for scanning, which incurs costs both in labor required to disassemble the machine and casing, and in non-productive down time for the machine.

BRIEF DESCRIPTION OF THE INVENTION

Described herein are a system and computer program product for in situ identification of internal components of a machine.

A first aspect of the disclosure provides a component identification system. The component identification system comprises a visual inspection device for obtaining an image of a data matrix code disposed on a surface of a component, and a computing device in signal communication with the visual inspection device, the computing device being configured to associate the data matrix code in the image with an identified component in a database. The visual inspection device is configured to be inserted into an internal environment in which the component is disposed.

A second aspect of the disclosure provides a computer program product comprising program code embodied in at least one computer-readable medium, which when executed, enables a computer system to implement a method of identifying a component. The method comprises decoding an image containing a data matrix code to identify the data matrix code in the image; and associating the data matrix code in the image with an identified component in a database.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

Figure 1:
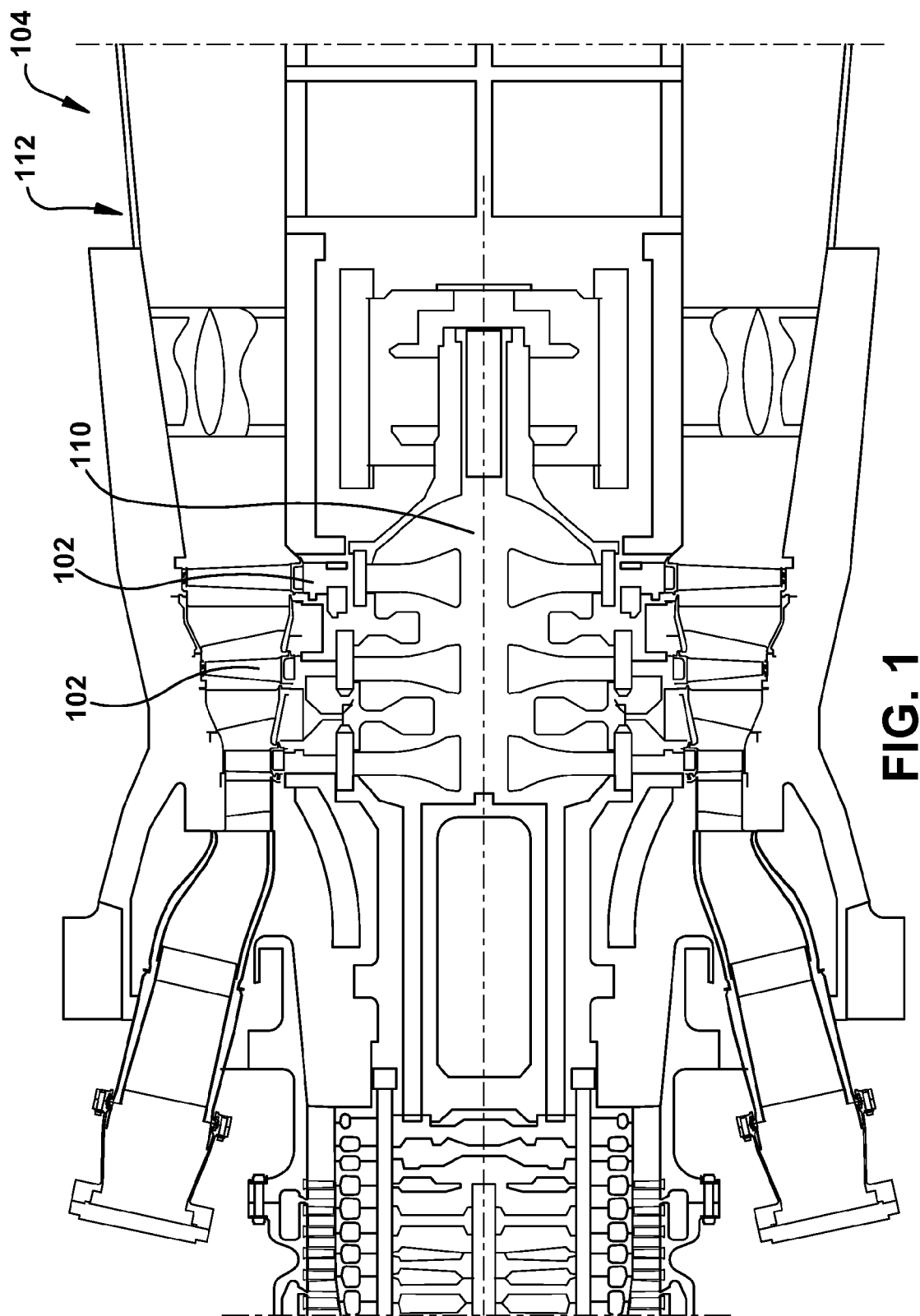
FIG. 1 shows a cross sectional illustration of an industrial machine in the form of a gas turbine.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

At least one embodiment of the present invention is described below in reference to its application in connection with the operation of a turbomachine. Although embodiments of the invention are illustrated and described relative to a turbomachine in the form of a gas turbine, it is understood that the teachings are equally applicable to other types of industrial machines including but not limited to aviation turbines, wind turbines, wind turbine gear boxes, steam turbines, generators, heat exchangers, aircraft engines, reciprocating engines, appliances, accessory bases, locomotive power train machines, healthcare machines such as MRI, CT, and x-ray machines, hydro turbine machines, electric motors, pumps, transformers, switchgears, and generator excitation equipment. Further, at least one embodiment of the present invention is described below in reference to a nominal size and including a set of nominal dimensions. However, it should be apparent to those skilled in the art that the present invention is likewise applicable to any suitable turbomachine and/or electric machine having an outer casing. Further, it should be apparent to those skilled in the art that the present invention is likewise applicable to various scales of the nominal size and/or nominal dimensions.

Figure 2:
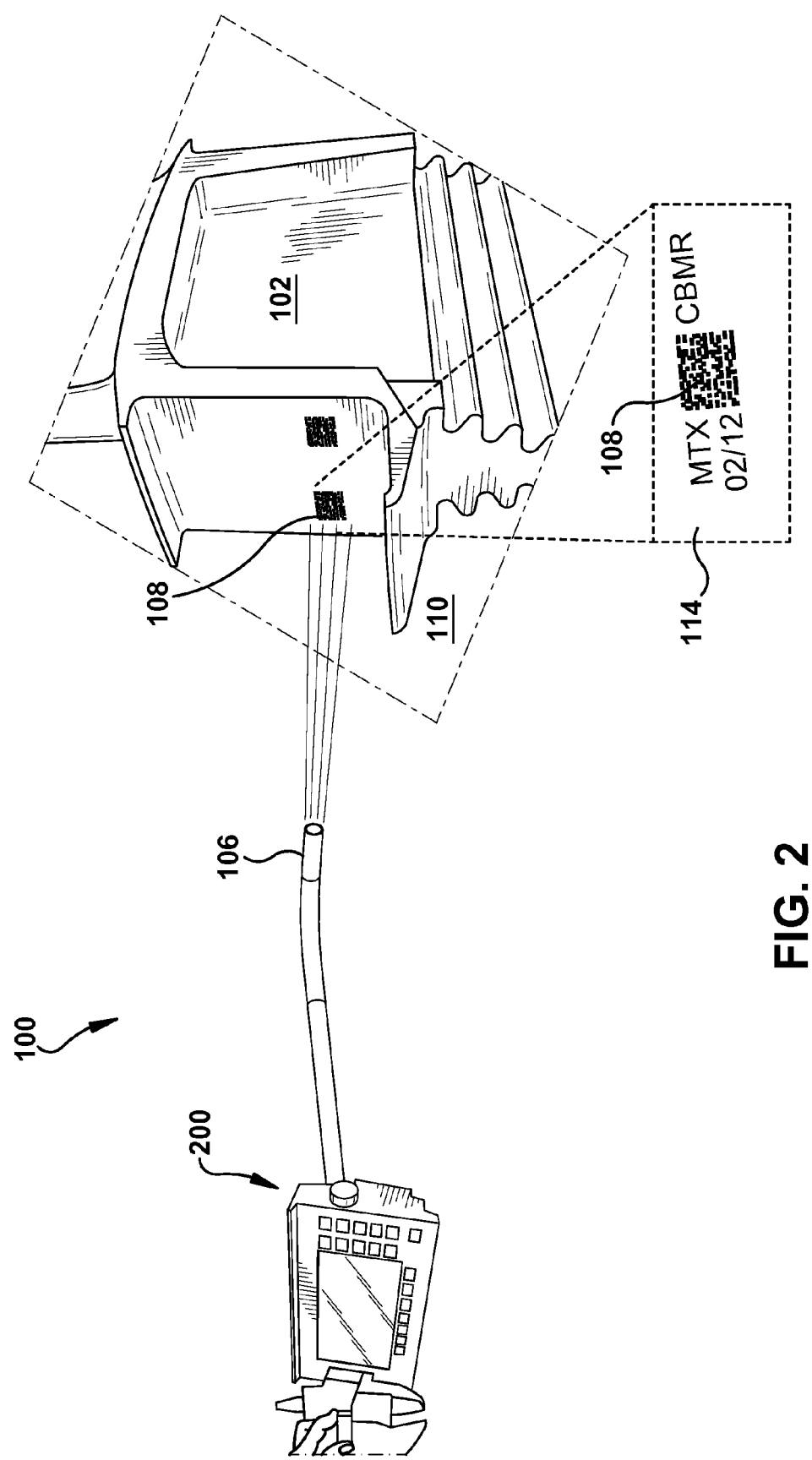
FIG. 2 shows an exploded schematic illustration of a component identification system in accordance with an embodiment of the disclosure.
Figure 3:
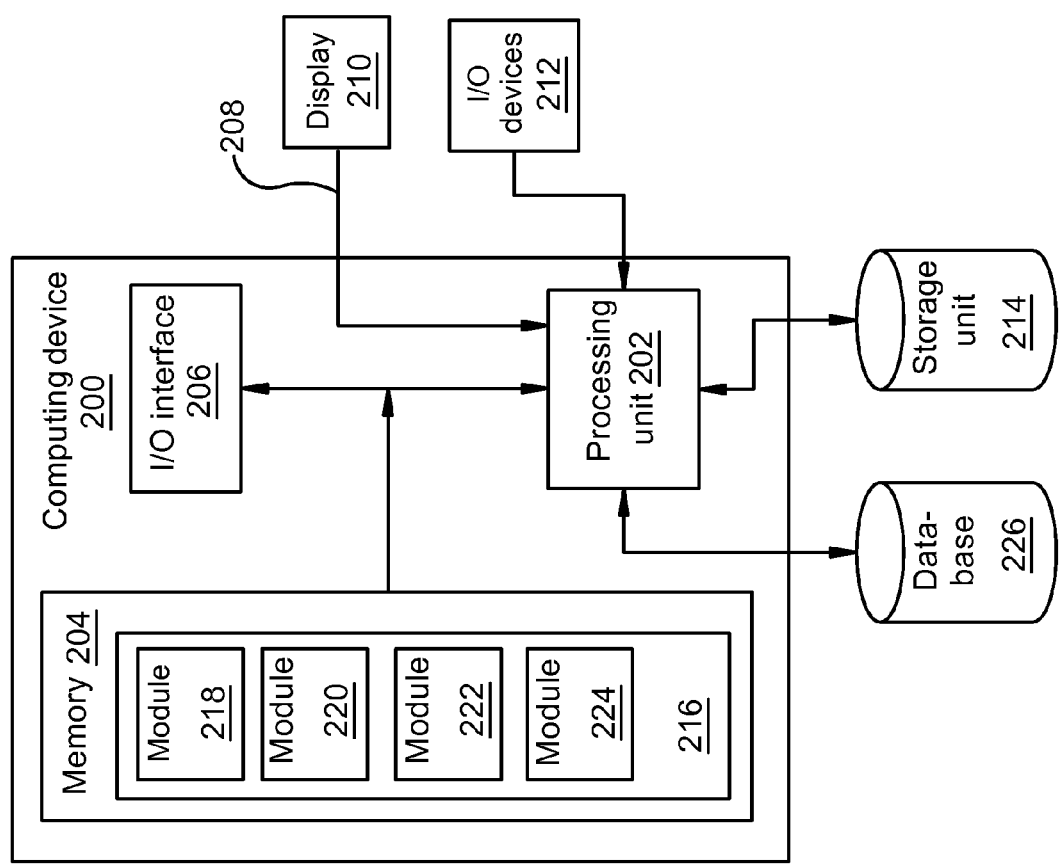
FIG. 3 shows a schematic diagram of a portion of the component identification system of FIG. 2, in accordance with an embodiment of the disclosure.

As indicated above, aspects of the invention provide, and FIGS. 1-3 illustrate a component identification system for identifying a component of an industrial machine in situ.

As shown in FIG. 2, component identification system 100 may include a visual inspection device 106 for obtaining an image 114 of a component identifier 108 disposed on a surface of component 102. Component 102 may be any type of component disposed on an interior of an industrial machine 104 (FIG. 1). For example, in certain non-limiting embodiments, industrial machine 104 may be a gas turbine as shown in FIG. 1, and component 102 may be a combustion component or a hot gas path component. Many other components 102 and types of industrial machines 104 are also contemplated. In various embodiments, component identifier 108 on component 102 may be a data matrix code (FIG. 2).

As shown in FIG. 2, visual inspection device 106 is configured to be inserted into an internal environment 110 of industrial machine 104 (FIG. 1) in which the component 102 is disposed. Internal environment 110 refers to the interior of industrial machine 104, which may be enclosed by casing 112 (FIG. 1). In various embodiments, visual inspection device 106 may be a borescope, although any type of visual inspection device capable of capturing clear, bright images may also be used. Visual inspection device 106 may be inserted into internal environment 110 in a number of ways as may be apparent to one of skill in the art, such as via a port in casing 112 (FIG. 1).

As further shown in FIG. 2, visual inspection device 106 may be in signal communication with computing device 200, such that after visual inspection device 106 obtains an image 114 of component identifier, it can be communicated to computing device 200 using a wired or wireless data communication protocol. Computing device 200 may receive the image via such communication protocol from visual inspection device 106.

As shown in FIG. 3, computing device 200 includes a processing unit 202, a memory 204, input/output (I/O) interfaces 206 operably connected to one another by pathway 208, which provides a communications link between each of the components in computing device 200. Further, computing device 200 is shown in communication with display 210, external I/O devices/resources 212, and storage unit 214, which may display, store, and manipulate respectively, data obtained by visual inspection device 106. I/O devices 212 can comprise one or more human I/O devices, such as a mouse, keyboard, joystick, or other selection device, which enable a human user to interact with computing device 200 and/or one or more communications devices to enable a device user to communicate with computing device 200 using any type of communications link.

In general, processing unit 202 executes computer program product 216 which provides the functions of computing device 200. These modules, including a decoding module 218, an association module 220, a tracking module 222, and a projection module 224 are stored in memory 204 and/or storage unit 214, and perform the functions and/or steps of the present invention as described herein. Memory 204 and/or storage unit 214 can comprise any combination of various types of computer readable data storage media that reside at one or more physical locations. To this extent, storage unit 214 could include one or more storage devices, such as a magnetic disk drive or an optical disk drive. Still further, it is understood that one or more additional components not shown in FIG. 3 can be included in computing device 200, including analysis of the data captured by visual inspection device 106 and transmitted in real time to computing device 200. Additionally, in some embodiments one or more external devices 212, display 210, and/or storage unit 214 could be contained within computing device 200 as shown in FIG. 2, rather than externally as shown in FIG. 3.

Computing device 200 can comprise one or more general purpose computing articles of manufacture capable of executing program code, such as program 216, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, program 216 can be embodied as any combination of system software and/or application software.

Further, program 216 can be implemented using a set of modules 218, 220, 222, 224. In this case, modules 218, 220, 222, 224 can enable computing device 200 to perform a set of tasks used by program 216, and can be separately developed and/or implemented apart from other portions of program 216. As used herein, the term "component" means any configuration of hardware, with or without software, which implements the functionality described in conjunction therewith using any solution, while the term "module" means program code that enables a computing device 200 to implement the actions described in conjunction therewith using any solution. When fixed in memory 204 or storage unit 214 of a computing device 200 that includes a processing unit 202, a module is a substantial portion of a component that implements the actions. Regardless, it is understood that two or more components, modules, and/or systems may share some/all of their respective hardware and/or software. Further, it is understood that some of the functionality discussed herein may not be implemented or additional functionality may be included as part of computing device 200.

When computing device 200 comprises multiple computing devices, each computing device can have only a portion of program 216 fixed thereon (e.g., one or more modules 218, 220, 222, 224). However, it is understood that computing device 200 and program 216 are only representative of various possible equivalent computer systems that may perform a process described herein. To this extent, in other embodiments, the functionality provided by computing device 200 and program 216 can be at least partially implemented by one or more computing devices that include any combination of general and/or specific purpose hardware with or without program code. In each embodiment, the hardware and program code, if included, can be created using standard engineering and programming techniques, respectively.

Regardless, when computing device 200 includes multiple computing devices, the computing devices can communicate over any type of communications link. Further, while performing a process described herein, computing device 200 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As noted, computing device 200 includes a decoding module 218 for decoding an image 114 containing a component identifier 108 to identify the component identifier 108 in the image 114 (FIG. 2). Decoding module 218 (FIG. 3) is capable of identifying the presence of a component identifier 108 in image 114, as well as identifying the specific component identifier 108 that is present (FIG. 2).

Computing device 200 may further include an association module 220 (FIG. 3) for associating the component identifier 108 in the image 114 (FIG. 2) that was identified by decoding module 218 (FIG. 3), with an identified component 102 in a database 226. In some embodiments, the associating may include associating the component identifier 108 in image 114 with various pieces of information about component 102, including but not limited to a serial number of component 102, a drawing number showing component 102, and an indication of any damage or defect previously present or otherwise associated with component 102. This associating may be carried out while component 102 remains in situ in internal environment 110, without opening casing 112 or disassembling industrial machine 104 (FIG. 1). This facilitates part level tracking of components 102 in the field without having to remove them from industrial machine 104.

Computing device 200 may further include a tracking module 222 (FIG. 3) for tracking the indication of any damage or defect associated with component 102. Users may use tracking module 222 to indicate components 102 that are found to have damage or defects present in an inspection with visual inspection device 106 (FIG. 2). This indication may be added to the record for the component 102, which includes information made available by computing device 200 to a user upon association of a component identifier 108 in an image 114 by association module 220. The indication may either be an indication of new damage to component 102 or an indication of additional or increased damage to a component 102 previously noted to have sustained some defect or damage. These damage or defect indications may further be used to track defective components 102 from one inspection to another, providing valuable information as to the location and status of damaged components.

Computing device 200 may further include a projection module 224 for projecting a future growth of damage to component 102 based on a plurality of inspections, and a rate of change in the amount of damage present on component 102 as tracked by tracking module 222. This projection may reduce the risk of forced outages and improve reliability of industrial machine 104 (FIG. 1).

Technical effects of the various embodiments of the present invention include the ability to identify an industrial machine 104 component 102 (FIG. 1) in situ based on a component identifier 108 (FIG. 2). A visual inspection device 106 is inserted into an internal environment 110 in an industrial machine 104, and is used to obtain an image 114 of a component identifier 108 on a surface of component 102. This image 114 may be received and decoded on a computing device 200, which associates the component identifier 108 in the image 114 with a particular component 102 in a database 226 (FIG. 3). The database entry for the particular identified component 102 may include various information about the component, thus allowing operators, repair personnel, and other related individuals to identify parts and access this information without disassembling the industrial machine 104 and removing component 102.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A component identification system comprising:
   a visual inspection device for obtaining an image of a data matrix code disposed on a surface of a component, wherein the visual inspection device is configured to be inserted into an internal environment in which the component is disposed; and
   a computing device in signal communication with the visual inspection device, the computing device being configured to associate the data matrix code in the image with an identified component in a database, wherein a record of the identified component in the database includes an indication of any damage or defect previously identified on the component; and
   wherein the computing device is further configured to track the indication of any damage or defect associated with the component over a plurality of inspections, and project a future growth of damage based on the plurality of inspections and a rate of change in the amount of damage present on the component.

2. The component identification system of claim 1, wherein the visual inspection device further comprises a borescope.

3. The component identification system of claim 1, wherein the internal environment comprises an interior of an industrial machine having a casing enclosing the interior of the industrial machine.

4. The component identification system of claim 3, wherein the industrial machine comprises one of: an aviation turbine, a gas turbine, a steam turbine, a heat exchanger, or an engine.

5. The component identification system of claim 1, wherein the component comprises one of a hot gas path component, a compressor component, or a combustion component of a gas turbine.

6. The component identification system of claim 1, wherein a record of the identified component in the database includes at least one of a serial number and a drawing number.

7. The component identification system of claim 1, wherein the computing device is further configured to indicate a presence of new damage in the record of the identified component.

8. A computer program product comprising program code embodied in at least one computer-readable medium, which when executed, enables a computer system to implement a method of identifying a component, the method comprising:
   decoding an image containing a data matrix code to identify the data matrix code in the image;
   associating the data matrix code in the image with an identified component in a database, wherein a record of the identified component in the database includes an indication of any damage or defect previously identified on the component;
   tracking the indication of any damage or defect associated with the component over a plurality of inspections; and
   projecting a future growth of damage based on the plurality of inspections and a rate of change in the amount of damage present on the component.

9. The computer program product of claim 8, further comprising receiving the image from a visual inspection device.

10. The computer program product of claim 9, wherein the receiving the image step further comprises receiving an image obtained using a borescope.

11. The computer program product of claim 9, wherein the associating of the data matrix code in the image with the identified component in the database further comprises associating the data matrix code with at least one of a serial number and a drawing number.

12. The computer program product of claim 8, wherein a source of the data matrix code in the image is disposed on a surface of the component.

13. The computer program product of claim 12, wherein the component comprises one of a hot gas path component, a compressor component, or a combustion component of a gas turbine.

14. The computer program product of claim 12, wherein the component is disposed in an internal environment, the internal environment comprising an interior of an industrial machine having a casing enclosing the interior of the industrial machine.

15. The computer program product of claim 14, further comprising obtaining the image using a visual inspection device, and
   wherein the associating includes associating the data matrix code in the image with the identified component in the database while the component remains in situ, without opening the casing.

16. The computer program product of claim 8, wherein the method further comprises: indicating a presence of new damage or defect in a record of the identified component when new damage is observed using the visual inspection device.

* * * * *